(12) United States Patent
Okamura et al.

(10) Patent No.: US 7,078,172 B1
(45) Date of Patent: Jul. 18, 2006

(54) SUBSTRATE ACTIVATION KIT AND METHOD FOR DETECTING DNA AND THE LIKE USING THE SAME

(75) Inventors: Hiroshi Okamura, Yamaguchi-ken (JP); Michifumi Tanga, Yamaguchi-ken (JP); Kaoru Yamakawa, Yamaguchi-ken (JP); Mitsuyoshi Ohba, Yamaguchi-ken (JP); Kenichi Takagi, Yamaguchi-ken (JP)

(73) Assignee: Toyo Kohan Co., Ltd., Tokyo (JP)

( * ) Notice: Subject to any disclaimer, the term of this patent is extended or adjusted under 35 U.S.C. 154(b) by 377 days.

(21) Appl. No.: 10/344,166

(22) PCT Filed: Jun. 20, 2001

(86) PCT No.: PCT/JP01/05246

§ 371 (c)(1),
(2), (4) Date: Aug. 20, 2003

(87) PCT Pub. No.: WO02/12891

PCT Pub. Date: Feb. 14, 2002

(30) Foreign Application Priority Data

Aug. 8, 2000 (JP) ............................... 2000-24096
Nov. 2, 2000 (JP) ............................ 2000-336640
Dec. 28, 2000 (JP) ............................ 2000-401867

(51) Int. Cl.
*C12Q 1/68* (2006.01)
*G01N 33/53* (2006.01)

(52) U.S. Cl. .................... 435/6; 435/7.1; 536/23.1; 536/24.3

(58) Field of Classification Search ............... 435/6; 536/23.1, 24.3
See application file for complete search history.

(56) References Cited

U.S. PATENT DOCUMENTS 5,656,462 A 8/1997 Keller et al.

FOREIGN PATENT DOCUMENTS

JP 8-500722 A 1/1996
WO WO 99/66322 12/1999

OTHER PUBLICATIONS

S. Löfås and B. Johnson "A novel maix on gold surfaces in surface plasmon resonance sensors for fast and efficient covalent immobilisation of ligands," J Chem. Soc.. Chem. Commun, 1526-1528 (1990).*
Silva Storri et al. "A Piezoelectric Biosensors for DNA Hybridisation Detection" *Analytical letters* 31(11);1795-1808 (1998).
Mengsu Yang et al. "Covalent Immobilization of Oligonucleotides on Modified Glass/Silicon Surfaces for Solid-phase DNA Hybridization and Amplification" *Chemistry Letter* :257-258 (1998).
Japan Patent Information Organization "Chemically Modified Border Brim and Method of Manufacturing for the Same" (2001-139532) Dialog File Number 347 Accession No. 6911996.

* cited by examiner

*Primary Examiner*—Ethan Whisenant
(74) *Attorney, Agent, or Firm*—Browdy and Neimark, PLLC

(57) ABSTRACT

It is intended to provide a method whereby DNA can be conveniently and rigidly immobilized on a substrate at such a high density as achieved by the conventional methods and a method of accurately detecting DNA. A substrate activation kit comprising a phosphate buffer (pH6), a solution A (an aqueous solution) of N-hydroxysuccinimide and a solution B (a dioxide solution) of 1-[3-(dimethylamino) propyl] 3-ethylcarbodiimide; and a method of detecting DNA characterized by comprising spotting DNA on a substrate having been activated by using the above activation kit and then hybridizing the spotted DNA with fluorescence labeled DNA.

11 Claims, 3 Drawing Sheets

SUBSTRATE ACTIVATION KIT AND METHOD FOR DETECTING DNA AND THE LIKE USING THE SAME

TECHNICAL FIELD

The present invention relates to a substrate activation kit useful in the fields of medical, biochemical and molecular biological researches, and also to a method for detecting a DNA or protein using said kit.

BACKGROUND ART

A gene analysis is useful in the fields of molecular biology and biochemistry, and employed recently also in a medical field, for example, to identify a disease.

Recently, a substrate on which a DNA had been immobilized was developed, and served to enable a substantial promotion of a gene analysis, which is applied also to the diagnosis of a disease in the medical field.

As a method for immobilizing a DNA on a substrate, a method was proposed wherein a polymer such as a polylysine is applied onto the surface of a glass slide or silicon substrate prior to the immobilization or wherein a semiconductor technology such as a photolithography is employed to synthesize a DNA on a substrate.

However, the method for immobilizing a DNA by applying a polymer such as a polylysine involves a problem due to the detachment of the DNA during a hybrid formation step and a washing step due to an unstable immobilization state of the DNA.

On the other hand, the method utilizing the semiconductor technology involves a problematically complicated manufacturing process which leads to an extremely high cost.

For the purpose of solving the problems mentioned above, we had already found that by modifying a substrate surface chemically to effect an activation by an active ester such as N-hydroxysuccinimide ester or p-nitrophenol ester a DNA can stably be immobilized.

Nevertheless, such a chemical modification requires a complicated procedure involving a large number of chemical reactions.

In addition, an activated substrate obtained by a chemical modification may allow any unwanted active points to be still remaining as they are even after spotting a DNA on the substrate.

Accordingly, such an unwanted active point, upon hybridizing a target DNA to the spotted DNA, allows the DNA to deposit also to itself, resulting in a problematic difficulty in detecting the DNA accurately.

Thus, an objective of the invention is to provide a method for immobilizing a DNA on a substrate in a simple manner but firmly at a high density as experienced in a conventional method and also a method for detecting a DNA and the like accurately, whereby overcoming the problems associated with conventional DNA immobilization methods described above.

DISCLOSURE OF THE INVENTION

We made an effort to accomplish the objective described above and finally discovered that a substrate can be activated simply by mixing two solutions.

It was also discovered that by masking any unwanted active points in a prehybridization step at a stage after activating a substrate and spotting a DNA or protein but before a hybridization the DNA or protein can accurately be detected, thus establishing the invention. It was also discovered that this masking can be omitted when the active groups have sufficiently been inactivated during the drying and washing procedures conducted in a work-up step after the spotting.

Furthermore, it was also discovered that by using a gel solution in an incubation step before a hybridization step or before a prehybridization step a DNA or protein can be detected with a further higher accuracy.

A substrate activation kit according to the invention comprises as major components a solution A consisting of a phosphate buffer (pH6) and N-hydroxysuccinimide and a solution B consisting of 1-[3-(dimethylamino)propyl]3-ethylcarbodiimide.

A substrate activation kit according to the invention is characterized by the second aspect wherein said solution A is an aqueous solution of a phosphate buffer (pH6) at 0.01 to 5 M and N-hydroxysuccinimide at 1 to 500 mM (0.115 to 57.5 g/L).

A substrate activation kit according to the invention is characterized by the third aspect wherein said solution B is a dioxane solution of 1-[3-(dimethylamino)propyl]3-ethylcarbodiimide at 0.05 to 10 M (9.59 to 1918 g/L).

A substrate activation kit according to the invention is characterized by the fourth aspect wherein 50 to 99% by volume of said solution A is employed together with 1 to 50% by volume of said solution B.

A method for detecting a DNA or protein according to the invention comprises performing, at a stage after spotting a DNA or protein onto a substrate which has been activated using an activation kit but before hybridizing a fluorescence labeled DNA to said spotted DNA or protein, a prehybridization for masking the substrate surface other than the spotting positions.

A method for detecting a DNA or protein according to the invention is characterized in that the prehybridization is effected by immobilizing a DNA or protein which is different from the DNA or protein spotted on the surface of the substrate.

A method for detecting a DNA or protein according to the invention comprises a substrate activation step using an activation kit, a spotting step for spotting a DNA or protein onto the activated substrate, a substrate incubation step or drying step after spotting, a prehybridization step for masking the substrate surface other than the spotting positions, a hybridization step for hybridizing a fluorescence labeled DNA to the spotted DNA or protein and a step for detecting the fluorescent positions in the hybridization positions.

A method for detecting a DNA or protein according to the invention is characterized in that the prehybridization step is a step for immobilizing a DNA or protein which is different from the DNA or protein spotted on the surface of the substrate.

BEST MODE FOR CARRYING OUT THE INVENTION

Figure 1:
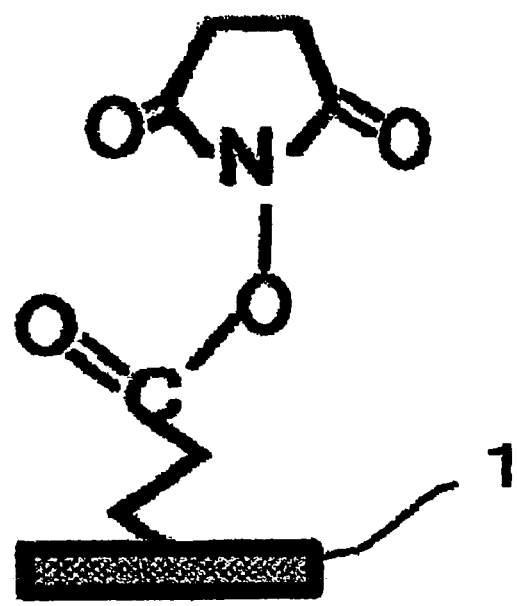
FIG. 1 shows a schematic view of a substrate whose surface is derivatized into an active ester.

The present invention is further described below.

(1) Substrate Preparation

A substrate employed in the invention has the characteristics which allow a DNA fragment, protein, peptide and the like to be immobilized on a substrate firmly without being washed off even when the substrate is washed and also allow a clear fluorescent spot to be observed upon irradiation with a fluorescent light, as a result of the procedure involving the formation of a surface treatment layer on a support such as a glass, plastic, silicon and the like followed by a chemical modification to attach a biological substance such as a DNA probe, protein, peptide and the like. The surface treatment layer is made preferably from diamond, soft diamond, carbon-based material or a mixture thereof or a laminate thereof. It may also be of a carbide such as hafnium carbide, niobium carbide, silicon carbide, tantalum carbide, thorium carbide, titanium carbide, uranium carbide, tungsten carbide, zirconium carbide, molybdenum carbide, chromium carbide, vanadium carbide and the like. The soft diamond mentioned here generally means an incomplete diamond structure which is a mixture of a diamond and a carbon such as a diamond-like carbon (DLC), regardless of the mixing ratio.

An example of such a substrate may be a substrate obtained by forming a film of a soft diamond on a glass slide.

In such a substrate, the thickness of the surface treatment layer ranges from 1 nm to 1000 nm.

In such a substrate, said diamond-like carbon is produced preferably by a ionization vapor deposition method in a gas mixture containing 1 to 99% by volume of a hydrogen gas and 99 to 1% by volume of a methane gas as a balance.

On the front and back sides of such a substrate, a monolayer of Ti, Au, Pt, Nb, WC and the like or a composite film thereof may be provided as a reflection layer. The thickness of the reflection layer is preferably 100 nm or more for the purpose of ensuring an entirely uniform coating film. More preferably, the thickness is 1000 nm or more.

It is also preferable that the surface of a glass substrate is imparted with a roughness intentionally within the range of Ra (JIS B 0601) from 1 nm to 1000 nm. Such a roughened surface is advantageous for immobilizing a large amount of DNA probes and the like at a higher density because it gives an increased surface area of the substrate.

The surface treatment layer of a substrate can be produced by a known method such as a microwave plasma CVD method, ECRCVD method, IPC method, direct current sputtering method, ECR sputtering method, ion plating method, arc ion plating method, EB vapor deposition method, resistance heating vapor deposition method, ionization vapor deposition method, arc vapor deposition method, laser vapor deposition method and the like.

A substrate may have a structure formed not only by providing a surface treatment layer on a substrate but also by binding a synthetic diamond, high pressure synthetic diamond, naturally occurring diamond, metal such as gold, silver, copper, aluminum, tungsten and the like, plastic such as a polycarbonate, fluoride resin and the like, a metal powder or ceramic powder together with a resin mixed as a binder. It is also possible that a starting material such as a metal powder or ceramic powder is compressed by a press molding machine and then sintered at a high temperature. A composite of a diamond with other material (for example a biphasic material) may also be employed.

The shape of a substrate body is not limited particularly and may be in the form of a plate, string, sphere, polygon, powder and the like.

The surface of a substrate body is further modified chemically for immobilizing a DNA or protein. An example of the chemical modification is an immobilization of a group having an active ester group at the terminal of a hydrocarbon chain on the surface of a support via an amide bond. Such a chemical modification promotes the immobilization of a biological substance such as a DNA, protein, peptide and the like on the surface of a substrate body. Otherwise, the chemical modification may be accomplished also by substituting the solid support surface with a hydrocarbon group having at its terminal a polar group such as a hydroxyl group, carboxyl group, epoxy group, amino group, thiol group, isocyanate group and the like.

Such a hydrocarbon group may for example be one having 1 to 12 carbon atoms, preferably 1 to 6 carbon atoms. Those which can be exemplified are a monocarboxylic acid such as formic acid, acetic acid, propionic acid and the like; a dicarboxylic acid such as oxalic acid, malonic acid, succinic acid, maleic acid, fumaric acid and the like; a polyvalent carboxylic acid such as trimellitic acid and the like. Among those listed above, oxalic acid and succinic acid are preferred.

A chemical modification can be accomplished for example by irradiating a support with an UV light in a chlorine gas to chlorinate the surface followed by irradiating with an UV light in an ammonia gas to effect an amination followed by a carboxylation using a suitable acid chloride or an acid anhydride. Alternatively, the chemical modification can be accomplished by an amination using a plasma in an ammonia gas instead of a chlorination of the surface, followed by a carboxylation using an acid chloride or acid anhydride.

(2) Activation Kit

An activation kit according to the invention consists of a solution A consisting of a phosphate buffer (pH6) and N-hydroxysuccinimide and a solution B (dioxane solution) consisting of 1-[3-(dimethylamino)propyl]3-ethylcarbodiimide.

It is also possible to use p-nitrophenol instead of N-hydroxysuccinimide.

According to an activation kit of the invention, a glass slide coated with a soft diamond (soft diamond-coated glass slide) into whose surface a carboxyl group has been introduced can be derivatized into an active ester using N-hydroxysuccinimide to obtain a substrate shown in FIG. 1.

Figure 2:
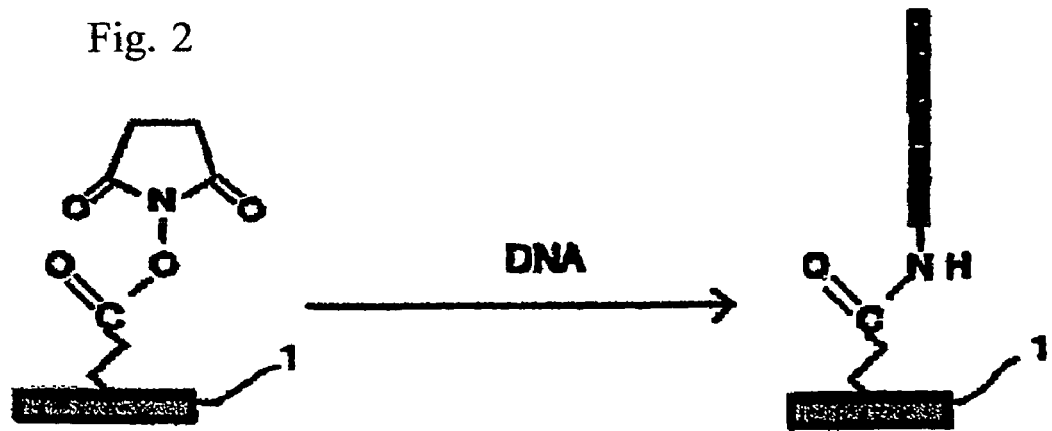
FIG. 2 shows the outline of the reactions for immobilizing a DNA on a substrate surface.

Thus, after activating the diamond surface, an amide bond with a primary amino group contained in a base of a DNA can be formed (see FIG. 2).

A solution A (aqueous solution) contains a phosphate buffer (pH6) at a concentration of 0.01 to 5 M while it contains N-hydroxysuccinimide at a concentration of 1 to 500 mM (0.115 to 57.5 g/L).

A phosphate buffer (pH6) can be prepared for example by providing a 0.1 M solution of potassium dihydrogen phosphate and a 0.1 M solution of dipotassium hydrogen phosphate and adding the solution of dipotassium hydrogen phosphate until pH 6 while monitoring the pH of the solution of potassium dihydrogen phosphate.

As a solution B (dioxane solution), a solution obtained by adding 1-[3-(dimethylamino)propyl]3-ethylcarbodiimide at a concentration of 0.05 to 10 M (9.59 to 1918 g/L) to dioxane is employed.

In an activation kit of the invention, a solution A and a solution B are present in a ratio so that 50 to 99% by volume of the solution A is combined with 1 to 50% by volume of the solution B.

After mixing solutions A and B in a container such as a beaker, a substrate is immersed in the mixed solution, and allowed to react for 5 to 120 minutes at 4 to 50° C. preferably with stirring. After derivatizing a carboxyl group on the surface of the substrate such as a soft diamond-coated glass slide into an active ester using N-hydroxysuccinimide, i.e. after activating the diamond surface, an amide bond with a primary amino group contained in a base of a DNA can be formed (FIG. 2). The substrate thus activated is washed for example with a sterilized water.

A substrate after activation is consumed as soon as possible in order to avoid any reduction in the activity. It is stored preferably in a desiccator after drying.

In the invention, a DNA can be detected via the following steps using a substrate which has been activated by an activation kit described above.

(3) Spotting Step

Onto a substrate which has been activated by an activation kit of the invention, a DNA is deposited as described below (spotting).

First, a DNA solution was prepared using a superpure water at a concentration of 0.01 to 10 μg/μL. While SSC, TE or the like can be used as a spotting buffer, a 1 to 50% formamide solution, a 1 to 50% glycerin solution or a 1 to 50% DMSO solution serves to accomplish a stable spotting due to a higher viscosity and also to avoid evaporation.

Figure 3:
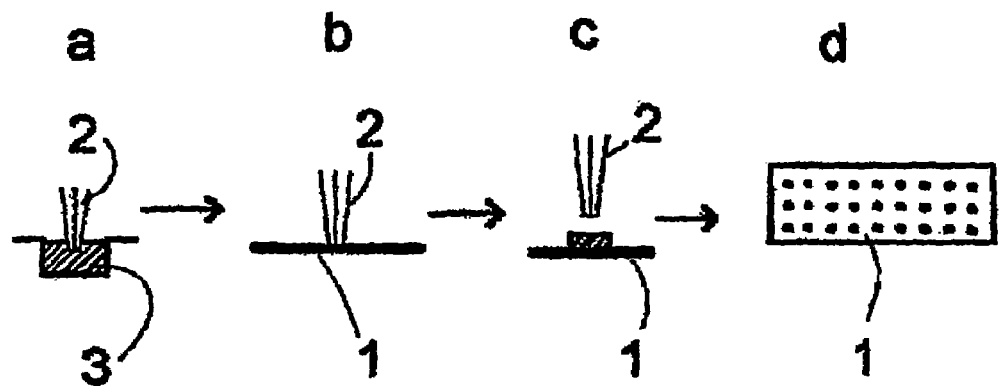
FIG. 3 shows a spotting process.

Subsequently, the spotting solution is spotted on the activated substrate using a spotter. The spotting solution here may be subjected to a heat degeneration or alkali degeneration to convert a double-stranded DNA into a single-stranded DNA followed by a rapid cooling. This spotting solution is drawn up for example as shown in FIG. 3 (a in FIG. 3) via a spotter needle, which is then pressed against the substrate (b) to apply the DNA solution on the substrate (c). In this manner, various types of DNAs are deposited on the glass slide surface (d).

(4) Incubation Step

Subsequently, an incubation is performed in order to proceed the reaction for immobilizing a spotted DNA on the surface of a substrate. Since the immobilization of a DNA on a substrate is a covalent bonding resulting from a chemical reaction, an incubation should be initiated immediately after the spotting for ensuring the advancement of the reaction.

Figure 4:
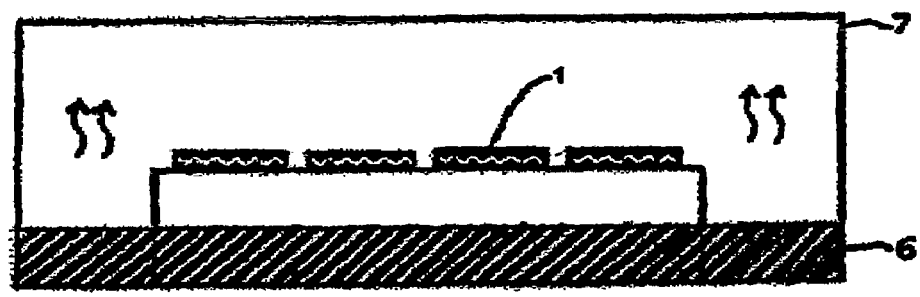
FIG. 4 shows the sectional view of a tight box.

While the incubation is conducted preferably under a highly humid condition, a tight box shown in FIG. 4 may for example be employed. In the tight box, a saturated NaCl solution is contained to give a humidity conditioned chamber whose humidity is kept at a constant level. For example, it is contained in an incubator set at 0 to 80° C. and allowed to stand until the temperature of the entire tight box becomes 0 to 80° C. Preferably, the temperature is 45 to 70° C. The saturated NaCl solution may be replaced for example with a 50% aqueous solution of formamide. Besides the NaCl solution, water or a potassium chloride solution may be employed.

While the temperature of an incubator may be 0 to 80° C., it is preferably 45 to 70° C. for promoting an immobilization reaction more satisfactorily.

Once the tight box became a humidity conditioned chamber, a spotted substrate is placed in, and incubated at a constant humidity.

It is preferable that the substrate is not in contact with the saturated NaCl solution or 50% aqueous solution of formamide. For example, the substrate can be mounted on a raised part of the bottom as shown in FIG. 4.

The incubation is continued preferably for 0.1 to 24 hours. After incubation, it is preferred to allow the substrate to stand in a thermostat chamber at 65 to 90° C. over a period of 1 hour or longer for drying.

Besides the method of the incubation in a highly humid atmosphere as described above, a method employing a gel solution can serve to enable a more stable and more promoted immobilization reaction. For example, as a component of the gel solution, a water-imbibing polymer such as agarose, gelatin, crosslinked polyethylene oxide and the like is preferred. As an additive, one having a blocking ability such as a protein including albumin, salmon sperm DNA, deoxyribonucleotide triphosphate, Denhart's solution is preferred. The concentration of the gel solution is preferably 0.01 to 99%. More preferably, it is 0.3 to 3%.

A resultant gel fragment is mounted on the position where a DNA was spotted, and can be allowed to undergo a further reaction in a humidity conditioned chamber set at 0 to 80° C. At this stage, it is preferred to dry the substrate in a thermostat chamber at 40 to 80° C. before mounting the gel, for the purpose of avoiding any leakage of the DNA.

After taking a substrate out of a humidity conditioned chamber, the substrate is washed. First, the substrate is immersed in a washing solution (for example, 2×SSC, 0.2% SDS) in a vat with the DNA-spotted side being facing up.

Subsequently, a washing is accomplished with shaking using a shaker and the like, and then the washing solution is replaced and the washing is repeated. After rinsing with a further dilute washing solution (for example 0.1×SSC), the substrate is dried using a centrifuge or air blower.

In a case where an incubation step was conducted using a gel solution containing an additive such as a protein, the subsequent prehybridization step can be omitted.

(5) Prehybridization Step

Subsequently, an incubated substrate is subjected to a pretreatment prior to a hybridization, i.e., prehybridization, for the purpose of masking any unwanted active points. Such a prehybridization may employ a bovine serum albumin (BSA), casein, salmon sperm DNA, Denhart's solution and the like, which may be combined with 20×SSC, SDS, formamide and the like to prepare a solution, which can be employed as a prehybridization solution. When the prehybridization solution contains a DNA such as a salmon sperm DNA, it is heated and then cooled rapidly to effect a heat degeneration for converting a double strand into a single strand.

A prehybridization solution may for example be a solution containing a Denhart's solution and formamide (5× Denhart's solution, 50% formamide).

On a position where a DNA has previously been spotted on a substrate, a prehybridization solution is added dropwise, and then a glass cover slip is mounted gently while avoiding any introduction of air bubbles.

A prehybridization is conducted preferably for a period of 0.1 to 24 hours.

It is preferred to conduct a prehybridization at a high humidity to prevent the prehybridization solution from being dried, and a humidity conditioned chamber such as one described in the section of (4) Incubation can be utilized.

Figure 5:
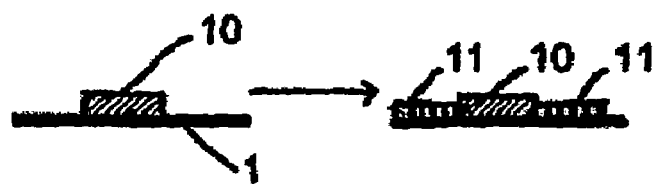
FIG. 5 shows a prehybridization process.

Once a tight box became a humidity conditioned chamber in an incubator set at 0 to 80° C., a soft diamond-coated glass slide is placed in while avoiding any contact with a saturated NaCl solution or 50% aqueous solution of formamide (slide being mounted on a raised part of the bottom) as in the step (4), and then the box is returned into the incubator. As a result, the glass slide surface other than the spotted positions are masked with a DNA independent of the DNA spotted previously on the substrate (FIG. 5).

Then, the substrate is washed. For example, the substrate is immersed in a 0.1×SSC solution and the glass cover slip is removed. Subsequently, the substrate is washed with a sterilized water using a shaker and the like, and then dried using a centrifuge or air blower.

This prehybridization step can be omitted in the case where, after an incubation step, a substrate is dried in a thermostat chamber at 30 to 80° C. for a period of 0.1 to 24 hours, and then washed thoroughly in a vat containing a washing solution (for example, 2×SSC, 0.2% SDS), rinsed with a rinsing solution (for example 0.1×SSC) and then dried whereby ensuring a complete hydrolysis and inactivation of any active esters. Nevertheless, it is preferable to conduct a prehybridization step for the purpose of obtaining reliable results, since a case of any insufficient inactivation allows a DNA to be immobilized on a position other than the spots in the following hybridization step.

(6) Hybridization Step

A target DNA sample is subjected to a procedure indicated in a fluorescence labeling kit, or to a reverse transcriptase reaction to effect a fluorescence labeling.

The fluorescence-labeled DNA sample thus obtained is combined with sterilized water, 20×SSC, SDS, formamide and the like, and stirred to prepare a hybridization solution.

At this stage, the DNA on the substrate is subjected to a heat degeneration when the DNA was spotted in the form of a double strand in the previous spotting step without conducting the heat degeneration or alkali degeneration of the spotting solution. A substrate which completed its step of (5) Prehybridization is immersed in a hot water for 3 to 5 minutes and then cooled on ice. This procedure can be omitted when a heat-degenerated or alkali-degenerated spotting solution was employed.

A resultant hybridization solution is added dropwise onto the position where a DNA was spotted on a substrate, and then a glass cover slip is mounted gently while avoiding any introduction of air bubbles.

It is also preferable to conduct a hybridization at a high humidity, and a humidity conditioned chamber described in the section of (4) Incubation can be utilized.

Once the tight box became a humidity conditioned chamber in an incubator set at 0 to 80° C., the substrate is placed in while avoiding any contact with a saturated NaCl solution or 50% formamide (substrate being mounted on a raised part of the bottom) as in the step (4), and then the box is returned to the incubator.

Figure 7:
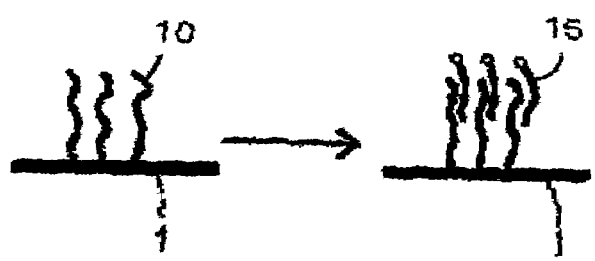
FIG. 7 shows a hybridization process.

As a result, a fluorescence labeled DNA is hybridized with a DNA which has already been spotted on a substrate, as shown in FIG. 7.

Finally, the substrate is washed. The washing is accomplished by removing a glass cover slip from the substrate using a 0.1×SSC solution followed by washing twice repetitively in a vat containing a washing solution (for example, 2×SSC, 0.2% SDS) followed by washing with a rinsing solution (for example 0.1×SSC) followed by drying using a centrifuge or air blower.

(7) Fluorescent Position Detection Step

A detection can be accomplished by reading the fluorescence label on a DNA hybridized with a DNA on the substrate surface using a fluorescent image reading scanner and the like.

EXAMPLES

Example 1

A protocol for using a soft diamond-coated glass slide is discussed below.

(1) Preparation of Soft Diamond-Coated Glass Slide

First, a glass slide was produced by forming a 25 nm-thick DLC film on the surface of a 25 mm-wide, 75 mm-long and 1 mm-thick glass by an ionization vapor deposition method using a gas mixture of 95% by volume of a methane gas and 5% by volume of a hydrogen gas.

Then, the surface of this glass slide was modified chemically.

Thus, the glass substrate surface was irradiated with a high pressure mercury lamp in an ammonia atmosphere for 10 minutes to effect an amination, and then the substrate was immersed in a solution of succinic anhydride in N-methylpyrrolidone for 60 minutes. As a result, a soft diamond-coated glass slide having a carboxyl group on the substrate surface was obtained.

The immobilization of a DNA on the soft diamond-coated glass slide was accomplished as shown in FIG. 1 after derivatizing the carboxy group on the surface into an active ester using N-hydroxysuccinimide.

The N-hydroxysuccinimide active ester group on the surface of the diamond was bound to a primary amino group contained in a base of a DNA via an amide bond (FIG. 2).

(2) Activation

An activation is performed using an activation kit. The compositions of the solutions in the activation kit was described below.

Solution A (Aqueous Solution)

Phosphate buffer (pH6): 0.1 M

N-Hydroxysuccinimide: 22 mM (2.5 g/L)

Solution B (Dioxane Solution)

1-[3-(dimethylamino)propyl]3-ethylcarbodiimide: 1M (191.8 g/L)

Then, a phosphate buffer (pH6) was prepared as described below.

First, a 0.1 M potassium dihydrogen phosphate solution (13.6 g/L) and a 0.1 M dipotassium hydrogen phosphate solution (17.4 g/L) are provided. The pH of the potassium dihydrogen phosphate solution is measured by a pH meter, and the dipotassium hydrogen phosphate solution is added with monitoring the pH until the pH became 6.

It is preferable to consume an activated substrate as soon as possible for avoiding any reduction in the activity. When stored, the substrate is dried at 65° C. for 30 minutes and then kept preferably in a desiccator.

The solution A is placed in a 90 ml beaker, to which 10 ml of the solution B was added. After stirring the solution thoroughly, the solution is placed in a dish, and a soft diamond-coated glass slide is immersed in this solution and allowed to stand at room temperature for 30 minutes (optionally with stirring using a stirrer such as a shaker, if any). An activated soft diamond-coated glass slide was washed twice with a sterilized water.

It is preferable to consume an activated substrate as soon as possible for avoiding any reduction in the activity. When stored, the substrate is dried at 65° C. for 30 minutes and then kept preferably in a desiccator.

On the other hand, a substrate can be activated without using an activation kit. In such a case, the following procedure is employed.

First, the substrate surface is activated. The following materials are provided.

Soft diamond-coated glass slide
1-[3-(Dimethylamino)propyl]3-ethylcarbodiimide
N-Hydroxysuccinimide
Potassium dihydrogen phosphate
Dipotassium hydrogen phosphate
Sterilized water Initially, an active ester derivatization (N-hydroxysuccinimide active ester derivatization of a carboxyl group) is conducted. The activation solution had the composition shown below.

N-Hydroxysuccinimide: 20 mM
1-[3-(Dimethylamino)propyl]3-ethylcarbodiimide: 0.1 M
Phosphate buffer (pH6): 0.1 M 959 mg of 1-[3-(dimethylamino)propyl]3-ethylcarbodiimide and 115 mg of N-hydroxysuccinimide were weighed into a 200 mL beaker, to which 50 mL of a phosphate buffer (pH6) was added to form a solution, in which a glass slide was immersed and allowed to react and then was washed in a manner analogous to that employing an activation kit described above.

(3) Spotting

Then a DNA was deposited on the activated substrate (so called spotting).

First, the following materials were provided.

Soft diamond-coated glass slide (activated)
DNA sample
Formamide
Sterilized water
Spotter A DNA sample was dissolved at 1 µg/µL in a 10% formamide solution (spotting buffer) to prepare a spotting solution. The spotting solution was subjected to a heat degeneration at 95° C. for 5 minutes and then cooled rapidly to 4° C. As shown in FIG. 3, the solution was drawn up via the spotter needle (a in FIG. 3), which is then pressed against the surface of the soft diamond-coated glass slide (b) to apply the DNA solution on the substrate (c). In this manner, a large number of spots were made on the glass slide surface (d).

(4) Incubation

A soft diamond-coated glass slide, saturated aqueous solution of NaCl, tight box and incubator were provided. The tight box containing the saturated aqueous solution of NaCl (for example a 1:1 solution mixture of water and formamide) was placed in the incubator set at 4° C., allowed to stand for about 1 hour to ensure that the temperature of the entire tight box became 4° C., whereby obtaining a humidity conditioned chamber.

Once the tight box became a humidity conditioned chamber, it was taken out of the incubator, and the soft diamond-coated glass slide was placed in the tight box while avoiding any contact with a saturated aqueous solution of NaCl (slide being mounted on a raised part of the bottom). Then the tight box was returned into the incubator, and allowed to stand for 1 hour, during which the temperature was adjusted to ensure a high humidity. The tight box containing the soft diamond-coated glass slide is shown in FIG. 4. A subsequent drying was accomplished using an oven at 80° C. for 3 hours.

(5) Prehybridization

The soft diamond-coated glass slide (which had been spotted and incubated), glass cover slip, salmon DNA, 20×SSC, 1×SSC, 10% SDS, formamide, sterilized water, 1.5 mL reaction tube, 200 µL eppendorf tube, vat, shaker, 200 mL beaker, air blower, saturated aqueous solution of NaCl, tight box and incubator were provided and the following procedure was conducted.

First, similarly to the procedure in the section of (4) Incubation described above, the tight box containing a saturated solution of NaCl was placed in an incubator set at 37° C., and allowed to stand for about 1 hour to ensure that the temperature of the entire tight box became 37° C., whereby obtaining a humidity conditioned chamber. Besides this, a prehybridization solution was prepared.

1 mg of a salmon DNA (which is a DNA independent of the sample) sample was weighed into a reaction tube and dissolved using 500 µL of sterilized water. Subsequently, 250 µL of 20×SSC, 50 µL of 10% SDS and 200 µL of formamide were added. After stirring, a required amount was weighed into an eppendorf tube, and employed as a prehybridization solution.

In this Example, 15 µL was employed per substrate when the spotting region was 1 cm×1 cm.

Subsequently, the prehybridization solution was subjected to a heat degeneration at 95° C. for 5 minutes, and then cooled rapidly to 4° C. Onto the DNA-spotted positions on the soft diamond-coated glass slide, the prehybridization solution was added dropwise, and a glass cover slip was mounted gently while avoiding any air bubbles being introduced. As a result, the surface of the glass slide other than the region spotted with the salmon DNA was masked (see FIG. 5).

Then, the tight box was taken out of the incubator, and the soft diamond-coated glass slide was placed in while avoiding any contact with a saturated aqueous solution of NaCl (substrate being mounted on a raised part of the bottom), and then the box is returned to the incubator and allowed to stand for 1 hour for ensuring the advancement of the reaction.

Figure 6:
FIG. 6 shows a washing step.

Then the washing was performed. The soft diamond-coated glass slide was taken out of the incubator, and the glass cover slip was removed in a 1×SSC solution contained in a 200 mL beaker. Then the slide was placed in the vat containing 1×SSC and 0.2% SDS with the surface being facing up, and shaken using a shaker for 5 minutes (FIG. 6). Subsequently, 1×SSC and 0.2% SDS were discarded and then 1×SSC and 0.2% SDS were added again, and shaken for 5 minutes. After washing again similarly with 1×SSC and 0.2% SDS, the substrate was rinsed gently with 0.1× SSC and made free of the solution on its surface using the air blower.

(6) Hybridization

The soft diamond-coated glass slide (prehybridized), glass cover slip, target DNA, 20×SSC, 1×SSC, 10% SDS, formamide, sterilized water, 200 µL eppendorf tube, vat, shaker, 200 mL beaker, air blower, fluorescence labeling kit, saturated aqueous solution of NaCl, tight box and incubator were provided.

First, the tight box containing the saturated aqueous solution of NaCl was placed in the incubator set at 37° C., and allowed to stand for about 1 hour to ensure that the temperature of the entire tight box became 37° C., whereby obtaining a humidity conditioned chamber.

Then, a DNA sample was labeled fluorescently. The fluorescence labeling was accomplished as directed by the fluorescence labeling kit or utilizing a reverse transcriptase reaction.

Subsequently, 2 µL of a 1 µg/µL fluorescence labeled DNA sample was taken into the reaction tube, to which 48 µL of the sterilized water was added. Thereafter, 25 µL of 20×SSC, 5 µL of 10% SDS and 20 µL of formamide were added, stirred, whereby obtaining a hybridization solution.

The hybridization solution was added dropwise to the soft diamond-coated glass slide, and the glass cover slip was mounted gently while avoiding any introduction of air bubbles. Then, the tight box was taken out of the incubator, and the glass slide described above was placed in while avoiding any contact with the saturated aqueous solution of NaCl (glass being mounted on a raised part of the bottom), and then the box is returned to the incubator and allowed to stand for 1 hour. As a result, the fluorescence labeled DNA was hybridized with the DNA which had previously been spotted on the substrate (see FIG. 7).

Finally, the washing was carried out. The substrate was taken out of the incubator, and the glass cover slip was removed in a 1×SSC solution contained in a 200 mL beaker. Then the substrate was placed in the vat containing 1×SSC and 0.2% SDS with the surface being facing up, and shaken using a shaker for 5 minutes. After washing again similarly with 1×SSC and 0.2% SDS, the substrate was rinsed gently with 0.1×SSC and made free of the solution on its surface using the air blower.

(7) Detection

The detection was accomplished by providing a fluorescent image reading scanner and reading the fluorescence label, as a fluorescent image, on the DNA hybridized with the DNA on the surface of the soft diamond-coated glass slide.

While the above description was in relation with the DNA detection, it is also possible to detect a protein instead of the DNA.

Example 2

A soft diamond-coated glass slide similar to that employed in Example 1 was activated similarly to Example 1. The spotting was conducted using the solutions similar to those in Example 1 except for employing 10% glycerin instead of formamide.

(4) Incubation

For the incubation, a tight box containing a saturated aqueous solution of NaCl was placed in an incubator set at 4° C., and allowed to stand for about 1 hour for ensuring that the temperature of the entire tight box became 4° C. The tight box was taken out of the incubator, and the substrate was placed in while avoiding any contact with the saturated aqueous solution of NaCl (substrate being mounted on a raised part of the bottom), and then the box is returned to the incubator and allowed to stand for 1 hour. The tight box containing the saturated aqueous solution of NaCl was placed in an incubator set at 65° C., allowed to stand for 1 hour, and then dried. After drying, the washing was performed using a buffer solution containing 20×SSC and 10% SDS. The prehybridization conducted in Example 1 was not conducted here.

(6) Hybridization

The soft diamond-coated glass slide (prehybridized), glass cover slip, target DNA, 20×SSC, 1×SSC, 10% SDS, formamide, sterilized water, 200 µL eppendorf tube, vat, shaker, 200 mL beaker, air blower, fluorescence labeling kit, saturated aqueous solution of NaCl, tight box and incubator were provided.

First, the tight box containing the saturated aqueous solution of NaCl was placed in the incubator set at 45° C., and allowed to stand for about 1 hour to ensure that the temperature of the entire tight box became 45° C., whereby obtaining a humidity conditioned chamber. The subsequent procedure was similar to that in Example 1.

The detection was made also similarly to Example 1. While the detection of a DNA was exemplified, it is also possible to detect a protein instead of the DNA.

Example 3

A soft diamond-coated glass slide similar to that employed in Example 1 was activated similarly to Example 1. The spotting was conducted using the solutions similar to those in Example 1 except for employing 10% glycerin instead of formamide.

(4) Incubation

For the incubation, a tight box containing a saturated aqueous solution of NaCl was placed in an incubator set at 4° C., and allowed to stand for about 1 hour for ensuring that the temperature of the entire tight box became 4° C. The tight box was taken out of the incubator, and the substrate was placed in while avoiding any contact with the saturated aqueous solution of NaCl (substrate being mounted on a raised part of the bottom), and then the box is returned to the incubator and allowed to stand for 1 hour. The tight box containing the saturated aqueous solution of NaCl was placed in an incubator set at 65° C., allowed to stand for 1 hour, and then dried. A 0.5% agarose gel was mounted on the substrate surface, and the substrate was placed in the tight box, which was then placed in a 45° C. incubator for 12 hours.

The washing was conducted using a buffer solution containing 20×SSC and 0.2% SDS followed by 0.1×SSC. The final washing was made with a 70% ethanol solution. The prehybridization conducted in Example 1 was not conducted here.

(6) Hybridization

The soft diamond-coated glass slide (prehybridized), glass cover slip, target DNA, 20×SSC, 1×SSC, 10% SDS, formamide, sterilized water, 200 µL eppendorf tube, vat, shaker, 200 mL beaker, air blower, fluorescence labeling kit, saturated aqueous solution of NaCl, tight box and incubator were provided.

First, the tight box containing the saturated aqueous solution of NaCl was placed in the incubator set at 45° C., and allowed to stand for about 1 hour to ensure that the temperature of the entire tight box became 45° C., whereby obtaining a humidity conditioned chamber. The subsequent procedure was similar to that in Example 1.

The detection was made also similarly to Example 1. While the detection of a DNA was exemplified, it is also possible to detect a protein instead of the DNA.

Example 4

A soft diamond-coated glass slide similar to that employed in Example 1 was activated similarly to Example 1. For the spotting, a superpure water was employed exclusively without adding formamide employed in Example 1.

(4) Incubation

For the incubation, a tight box containing a 50% aqueous solution of formamide was placed in an incubator set at 60° C., and allowed to stand for about 1 hour for ensuring that the temperature of the entire tight box became 60° C. The tight box was taken out of the incubator, and the substrate was placed in while avoiding any contact with the 50% aqueous solution of formamide (substrate being mounted on a raised part of the bottom), and then the box is returned to the incubator and allowed to stand for 3 hours. After washing with a buffer solution containing 20×SSC and 0.2% SDS followed by 0.1×SSC, the substrate was rinsed with sterilized water and then dried using an air blower. Then a prehybridization solution (5× Denhart's solution, 50% formamide) was added dropwise to the substrate, and the glass cover slip was mounted gently while avoiding any introduction of air bubbles. The tight box was taken out of the incubator set at 60° C. and the substrate was placed in while avoiding any contact with the 50% formamide. The tight box containing the substrate was placed in the incubator set at 60° C. whereby effecting the prehybridization for 1 hour.

The glass cover slip was washed off using 0.1×SSC and the substrate was washed with a sterilized water for 15 minutes. Thereafter, the solution on the surface was blown off using an air blower.

(6) Hybridization

The soft diamond-coated glass slide (prehybridized), glass cover slip, target DNA, 20×SSC, 1×SSC, 10% SDS, formamide, sterilized water, 200 µL eppendorf tube, vat, shaker, 200 mL beaker, air blower, fluorescence labeling kit, 50% aqueous solution of formamide, tight box and incubator were provided.

First, the tight box containing the 50% aqueous solution of formamide was placed in the incubator set at 45° C., and allowed to stand for about 1 hour to ensure that the temperature of the entire tight box became 45° C., whereby obtaining a humidity conditioned chamber. The subsequent procedure was similar to that in Example 1.

The detection was made also similarly to Example 1. While the detection of a DNA was exemplified, it is also possible to detect a protein instead of the DNA.

INDUSTRIAL APPLICABILITY

By using an activation kit of the invention, which involves preparation of a solution A and solution B, a substrate can conveniently and rapidly be activated, since only a single stage reaction is enough to activate the substrate.

Also according to a method for detecting a DNA or protein of the invention, which involves a prehybridization, an accurate DNA detection is possible without allowing the DNA to deposit also to any unwanted active point.

In addition, an incubation using a gel solution enables a stable and promoted immobilization reaction, which leads to an accurate detection of a DNA or protein.

Accordingly, the present invention is useful in various fields such as diagnosis of a disease in the medical field, and biochemical and molecular biological researches.

The invention claimed is:

1. A substrate activation kit comprising as major components a solution A consisting of a phosphate buffer (pH6) and N-hydroxysuccinimide and a solution B consisting of 1-[3-(dimethylamino)propyl]3-ethylcarbodiimide.

2. An activation kit according to claim 1 wherein said solution A is an aqueous solution of a phosphate buffer (pH6) at 0.01 to 5 M and N-hydroxysuccinimide at 1 to 500 mM (0.115 to 57.5 g/L).

3. An activation kit according to claim 1 or claim 2 wherein said solution B is a dioxane solution of 1-[3-(dimethylamino)propyl]3-ethylcarbodiimide at 0.05 to 10 M (9.59 to 1918 g/L).

4. An activation kit according to claim 1 containing 50 to 99% by volume of said solution A and 1 to 50% by volume of said solution B.

5. A substrate activation kit according to claim 1 wherein said substrate is a substrate obtained by a chemical modification of a glass slide having a surface treatment layer of a diamond-like carbon.

6. A substrate activation kit according to claim 1 or claim 5 wherein said chemical modification is characterized by providing a hydroxyl group, carboxyl group, epoxy group and amino group at a terminal.

7. A substrate activation kit according to claim 1 wherein said chemical modification is characterized by subjecting said substrate to a plasma amination in an ammonia gas.

8. The activation kit according to claim 2 containing 50 to 99% by volume of said solution A and 1 to 50% by volume of said solution B.

9. The activation kit according to claim 3 containing 50 to 99% by volume of said solution A and 1 to 50% by volume of said solution B.

10. A substrate activation kit according to claim 5 wherein said chemical modification is characterized by subjecting said substrate to a plasma amination in an ammonia gas.

11. A substrate activation kit according to claim 6 wherein said chemical modification is characterized by subjecting said substrate to a plasma amination in an ammonia gas.

* * * * *